US00PP17935P2

(12) United States Plant Patent
Danziger

(10) Patent No.: US PP17,935 P2
(45) Date of Patent: Aug. 21, 2007

(54) ***TORENIA* PLANT NAMED 'DANMOON14'**

(50) Latin Name: ***Torenia* sp.**
Varietal Denomination: DANMOON14

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/357,981

(22) Filed: Feb. 22, 2006

(51) Int. Cl.
*A01H 5/00* (2006.01)

(52) U.S. Cl. ..... Plt./263
(58) Field of Classification Search ..... Plt./263
See application file for complete search history.

(56) References Cited
PUBLICATIONS
European Union Community Plant Variety Office (CPVO)—Application No. 2005/2543 filed Dec. 1, 2005—documents include copy of filing receipt dated Dec. 8, 2005 (2 pgs.); and Technical Questionnaire (5 pgs.).

*Primary Examiner*—Kent Bell
*Assistant Examiner*—Annette H Para
(74) *Attorney, Agent, or Firm*—Foley & Lardner, LLP

(57) ABSTRACT

A new and distinct *Torenia* plant named 'DANMOON14' characterized by having shiny green foliage, doted with plenty of delicate, funnel form, cup-shaped flowers with petals in shades of violet, purple and light purple with a yellow blotch on lower petal; vigorous growth habit; densely, compact branching habit which gracefully semi-cascading from hanging baskets; early flowering response and stays in full bloom in moderate climate; suitable as an annual for hanging pots outdoors under partial shade; and good weather tolerance with a preferred temperature range of 15° C. to 25° C.

2 Drawing Sheets

Latin name of the genus and species of the plant claimed: *Torenia* sp.
Variety denomination: 'DANMOON14'.

BACKGROUND OF THE INVENTION

The present invention relates to a new and distinct cultivar of *Torenia* plant, botanically known as *Torenia* sp. of the *Scrophulariaceae* family, and hereinafter referred to by the cultivar name 'DANMOON14'.

The new *Torenia* cultivar originated from a cross made in a controlled breeding program by the inventor Gabriel Danziger, in (2002) in Moshav Mishmar Hashiva, Israel. The female or seed parent is the *Torenia* cultivar designated 'TR-2-1001' (unpatented). The male or pollen parent is the *Torenia* cultivar designated 'TR-1' (unpatented). DANMOON14 The new *Torenia* cultivar 'DANMOON14' was discovered and selected by the inventor Gabriel Danziger, as a single flowering plant within the progeny of the stated cross in a controlled environment in (2002) in Moshav Mishmar Hashiva, Israel.

Asexual reproduction of the new *Torenia* cultivar by soft tip cuttings was first performed in July of 2002 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'DANMOON14' which in combination distinguish this *Torenia* as a new and distinct cultivar:

1. Plants produce shiny green foliage, doted with plenty of delicate, funnel form, cup-shaped flowers with petals in shades of violet, purple and light purple with a yellow blotch on lower petal;
2. Vigorous growth habit;
3. Densely, compact branching habit which gracefully cascades from hanging baskets;
4. Early flowering response and stays in full bloom in moderate climate;
5. Suitable as an annual for hanging pots outdoors under partial shade; and
6 . Good weather tolerance with a preferred temperature range of 15° C. to 25° C.

Plants of the new *Torenia* cultivar 'DANMOON14' differ from plants of the parents, 'TR-2-1001' (unpatented) and 'TR-1' (unpatented), in the following characteristics described in Table 1.

TABLE 1

| Character | New Cultivar 'DANMOON14' | Female Parent 'TR-2-1001' (unpatented) |
|---|---|---|
| Mature Flower Color | Petal shades of violet, purple, and light purple, with a yellow blotch on lower petal | Petal shades of (pink), with a (yellow) blotch on lower petal |
| Flower size | Depth: About 3.2 cm<br>Width: About 2.8 cm | Depth: About 3.5 cm<br>Width: About 3.2 cm |
| Growth habit | Bush, semi-cascading | Bush, trailing |
| Flowering time | 3 weeks from planting | 6 weeks from planting |

| Character | Male Parent 'TR-1' (unpatented) |
|---|---|
| Mature Flower Color | Petal shades of (pink), with a (yellow) blotch on lower petal |

TABLE 1-continued

| | | |
|---|---|---|
| | Flower size | Depth: About 2.8 cm<br>Width: About 3.0 cm |
| | Growth habit | Bush |
| | Flowering time | 2 weeks from planting |

Of the many commercial cultivars known to the present inventor, the most similar in comparison to the new *Torenia* cultivar 'DANMOON14' is the *Torenia* cultivar 'DANTOHONEYMON' (unpatented, and disclosed in U.S. Pat. No. 11,187), in the following characteristics described in Table 2:

TABLE 2

| Characteristic | New Cultivar 'DANMOON14' | Comparison Cultivar 'DANTOHONEYMON' (unpatented) |
|---|---|---|
| Mature Flower Color | Petal shades of violet, purple, and light purple, with a yellow blotch on lower petal | Petal shades of red-purple, and purple, with a yellow blotch on lower petal |
| Flower size | Depth: About 3.2 cm<br>Width: About 2.8 cm | Depth: About 3.0 cm<br>Width: About 3.0 cm |
| Growth habit | Bush, semi-cascading | Bush, cascading |
| Flowering time | 8 weeks from planting | 9 weeks from planting |

BRIEF DESCRIPTION OF THE PHOTOGRAPHS

The accompanying photographs illustrate the overall appearance of the new *Torenia* cultivar 'DANMOON14' showing the colors as true as is reasonably possible with colored reproductions of this type. Colors in the photographs may differ slightly from the color values cited in the detailed botanical description, which accurately describe the color of 'DANMOON14'.

DETAILED BOTANICAL DESCRIPTION

Figure 1:
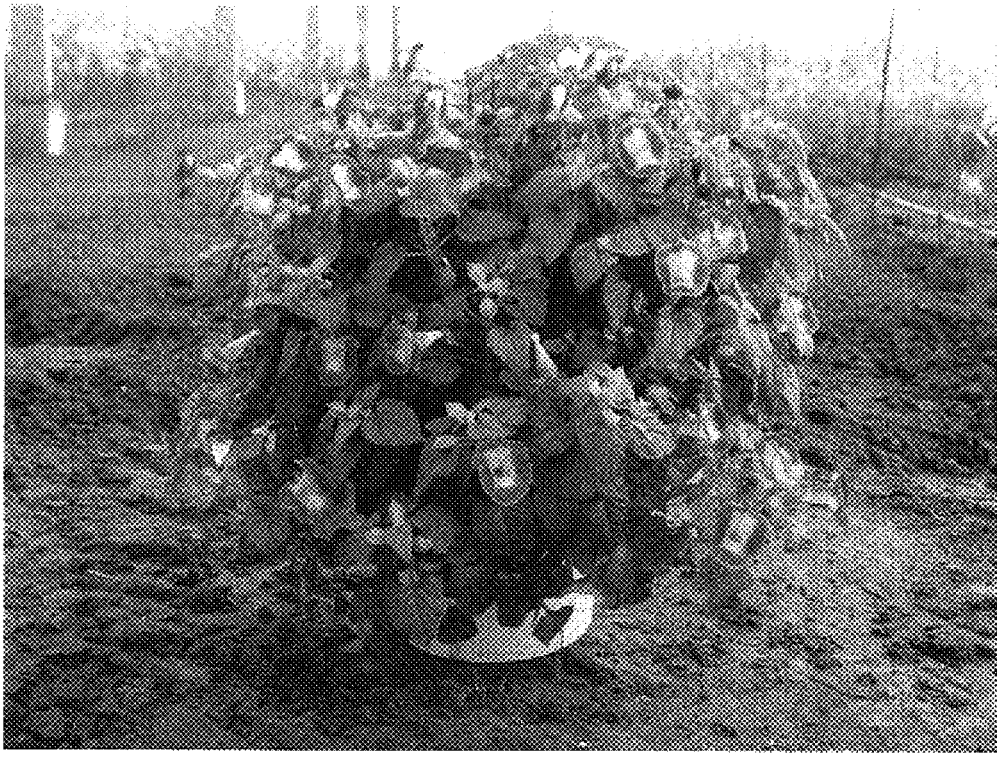
FIG. 1 shows a side perspective view of a typical flowering plant of 'DANMOON14' in a hanging planter at 3 months of age.
Figure 2:
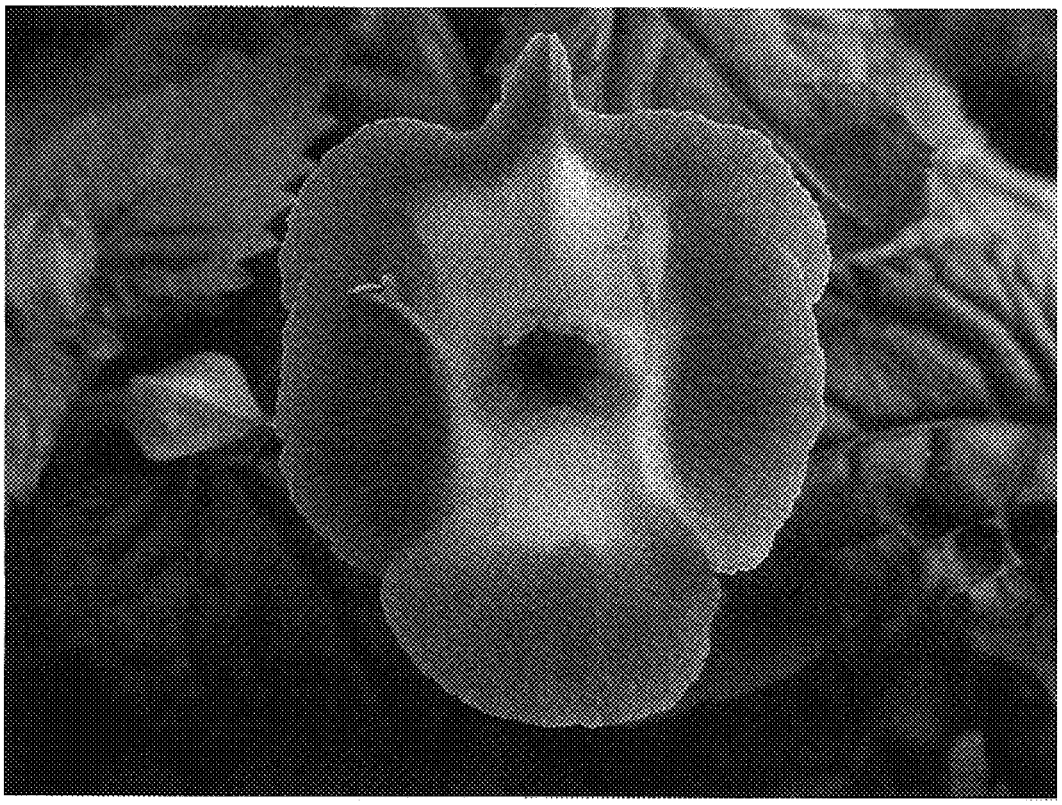
FIG. 2 shows a close-up of the typical flowers, buds and leaves of 'DANMOON14' at 3 months of age.

The new *Torenia* cultivar 'DANMOON14' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANMOON14' as grown in a greenhouse in Moshav Mishmar Hashiva, Israel, under conditions which closely approximate those generally used in commercial practice. Optimal growth conditions include that plants of 'DANMOON14' are grown outdoors in a moderate climate and indoors during the winter season. Irrigation and fertilization are recommended on a regular basis. Plants of 'DANMOON14' are usually grown in full sunlight, but partial shade is required in mid summer. Plants of 'DANMOON14' are fully grown in 3 months from planting a cutting in the summer season and bloom all year-round in a moderate climate. The 'DANMOON14' plants describe herein were grown indoors in 16 cm pots in a glass greenhouse in Moshav Mishmar Hashiva, Israel, with the day temperatures ranging from 18° C. to 35° C. and night temperatures ranging from 16° C. to 25° C. Plants of 'DANMOON14' were fertilized up to a level of 59 ppm N, 35.4 ppm P and 94.4 ppm K.

Color references are made to The Royal Horticultural Society Colour Chart (R.H.S.), 2001 edition, except where general colors of ordinary significance are used. Color values were taken under daylight conditions at approximately 12:00 noon in June of 2004 in Moshav Mishmar Hashiva, Israel. The age of the plant describe is 3 months.

Classification:
- *Botanical.*—*Torenia* sp.
- *Commercial.*—*Torenia* cultivar Roslyn Moon.

Parentage:
- *Female or seed parent.*—*Torenia* cultivar designated 'TR-2-1001' (unpatented).
- *Male or pollen parent.*—*Torenia* cultivar designated 'TR-1' (unpatented).

Propagation: Tissue culture (micropropagation of young in vitro plantlet) and soft tip cuttings.

Plant:
- *Form.*—Bush, semi-cascading.
- *Growth habit.*—Rounded and compact.
- *Height.*—About 15 to 25 cm.
- *Spread.*—About 40 cm.
- *Cold tolerance.*—Frost tender. Temperature below 5° C. may damage plants.
- *Vigor.*—Vigorous growth; plants are fully grown in 3 months from planting a cutting in summer.

Stem:
- *Color.*—Yellow-Green, RHS 144A.
- *Length.*—15 to 20 cm maximum length.
- *Diameter.*—About 0.3 cm.
- *Pubescence.*—Minimal and sporadic; stem is quadrangular, few hairs on the edges.
- *Branching.*—About 5 to 9 main branches grow from the base and split into hundreds of secondary and tertiary branches.
- *Length of Internodes.*—1.5 to 3.0 cm.

Foliage:
- *Overall shape.*—Convex, deltoid.
- *Apex.*—Reniform.
- *Base.*—Cordate.
- *Size of leaf.*—Length: About 3.8 cm. Width: About 3.0 cm.
- *Margin.*—Serrate.
- *Color.*—Center color of leaf: Green, RHS 137A. Upper side: Green, RHS 137A. Under side: Yellow-Green, RHS 146B.
- *Leaf texture.*—Minimal pubescence present.
- *Venation.*—Pattern: Pinnate, mid-rib splits to 4 to 6 veins. Color: Yellow-green, RHS 146B.
- *Petioles.*—Length: About 1 to 1.3 cm. Diameter: About 0.25 cm. Color: Yellow-Green, RHS 146B.

Flowers:
- *Blooming period.*—All year round in a moderate climate or in a greenhouse environment. In Israel, flowering occurs between February and November outdoors.
- *Flowering response time.*—8 weeks from plants in summer season.
- *Flowering stem.*—Flowers appear along the growing stems.
- *Quantity of flowers.*—Per stem: About 3 to 5; Per plant: About 150 to 500.

*Flowering longevity.*—On the plant: about 4 to 7 days, depending on temperature; Vase life: about 2 to 4 days.

*Type.*—Single.

*Shape.*—Overall: funnel form; 5-winged. Corolla tube: cylindrical or often broadened above; Corolla: 2-lipped, the upper lip faintly 2-lobed, the lower lip 3-lobed.

*Orientation at opening.*—Slanted upward.

*Fragrance.*—None.

*Flower size.*—Depth: About 3.2 cm. Width: About 2.8 cm.

*Buds.*—Shape: Oblong, cylindrical, ellipsoidal, 5-winged. Size: Length: About 1.6 cm. Diameter: About 0.9 cm. Color: Yellow-green, RHS 144A. Texture: Pubescence on winged edges.

*Floral tube.*—Length: About 2.5 cm. Color: The colors change going through the flower tube down. Outside: Violet, RHS 84A (apex), light purple, RHS 76A (middle) and purple, RHS N78A middle and RHS 12A (base). Inside: Light purple, RHS 76B (apex) and yellow-orange, RHS 14A (base).

*Petals.*—Number: Four, fused. Length: Upper Petal: About 2.5 cm; Side Petals: About 2.0 cm; Lower Petal: About 2.0 cm. Width: Upper Petal: About 1.5 cm; Side Petals: About 1.1 cm; Lower Petal: About 1.5 cm. Shape: Upper Petal: Overall: orbicular, Apex: rounded, Base: fused; Side Petals: Overall spatulate, Apex: rounded, Base: fused; Lower: Overall: spatulate, Apex: rounded, Base: fused. Margin: Entire and undulated. Color: Violet petals with purple blotches on side petals surrounding the corolla, and a yellow blotch in the middle of the lower petal near base, and light purple color at base of all petals.

*Mature petals.*—Please review carefully, insert missing any RHS designation and confirm accuracy of listed colors and their specified location. Upper Surface: Upper Petal: Near apex, violet, RHS 84A, and near base, light purple, RHS 76A; and margin, RHS 84A; Side Petals: Near apex, violet, RHS 84A, with centralized purple blotch, RHS N78A, and near base, light purple, RHS 76A, and margin RHS 84A; Lower Petal: Primarily violet, RHS 84A, with yellow blotch, RHS 7A, in the middle near base, and light purple color surrounding yellow blotch and near base, RHS 76A, and margin RHS 84A. Lower Surface: Upper Petal: Near apex, RHS 84A, and near base, RHS 76A and margin, RHS 84A; Side Petals: Near apex, RHS 85A, and near base, RHS 85B and margin, RHS 84A; Lower Petal: Near apex, RHS 85B, and near base, RHS 158A and margin, RHS 85C. Throat: Upper throat: Light purple, RHS 76B; Lower throat: Yellow-orange, RHS 14A.

*Immature petals.*—Upper Surface: Upper Petal: Near apex, RHS 76A, and near base, RHS 76A; and margin, RHS N80B; Side Petals: Near apex, RHS N80A, near base, RHS N80A, and margin RHS N80C; Lower Petal: Primarily RHS N80A, with yellow blotch, RHS 7A, in the middle near base, and margin RHS N80A. Lower Surface: Upper Petal: Near apex, RHS N80C, and near base, RHS N80C N80B and margin, RHS N80C; Side Petals: Near apex, RHS N80A, and near base, RHS N80B and margin, RHS N80A; Lower Petal: Near apex, RHS N80B, and near base, RHS 158A and margin, RHS N80B; Throat: Upper throat: Light purple, RHS 76A; Lower throat: Yellow, RHS 13A.

*Sepals.*—Number: 5. Length: About 1.7 cm. Width: About 1 cm. Shape: Two-lobed, 5-winged. Apex: Acute. Base: Wedge shaped. Margin: Entire. Color: Yellow-green, RHS 144A.

*Peduncle.*—Length: About 1.4 to 2 cm. Diameter: About 0.2 mm. Texture: Smooth. Color: Yellow-Green, RHS 144A.

Reproductive organs:

*Androecium.*—Stamen: Number: 2 pairs per flower; fused. Color: Purple, RHS 76 D. Anther: Length: About 0.4 cm; upper anther 0.4 cm. Width: About 0.05 cm. Color: Purple, RHS 76 D. Spur: Present. Filament. Length: About 1.4 cm; lower filaments are shorter 0.3 cm. Width: About 0.05 cm. Color: Purple, RHS 76D. Pollen: Amount: Sparse. Color: White, RHS N155C. Requirements for pollination: Young flowers, vital pollen, and receptive, open stigma.

*Gynoecium.*—Pistil: Number: One per flower. Length: About 2.1 cm. Stigma: Shape: Two lobes, open to opposite sides, deltoid shape. Length: About 0.2 cm. Width: About 0.2 cm. Color: Purple, RHS 76B. Style: Length: About 1.7 cm. Color: Purple, RHS 76C. Ovary: Number: 1. Length: About 0.5 cm. Width: About 0.2 cm. Color: Green, RHS 143A.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'DANMOON14', substantially as illustrated and described herein.

* * * * *